(12) United States Patent
Chen et al.

(10) Patent No.: US 7,183,425 B2
(45) Date of Patent: Feb. 27, 2007

(54) DIASTEREOSELECTIVE REDUCTIVE AMINATION PROCESS

(75) Inventors: Cheng Yi Chen, Plainsboro, NJ (US); Paul N. Devine, Tinton Falls, NJ (US); Bruce S. Foster, Scotch Plains, NJ (US); Greg Hughes, Beaconsfield (CA); Paul O'Shea, Westmount (CA)

(73) Assignee: Merck Frosst Canada Ltd., Quebec (CA)

(*) Notice: Subject to any disclaimer, the term of this patent is extended or adjusted under 35 U.S.C. 154(b) by 19 days.

(21) Appl. No.: 11/193,798

(22) Filed: Jul. 29, 2005

(65) Prior Publication Data

US 2006/0030731 A1   Feb. 9, 2006

Related U.S. Application Data

(60) Provisional application No. 60/598,603, filed on Aug. 4, 2004.

(51) Int. Cl.
*C07C 229/00* (2006.01)
(52) U.S. Cl. ..................................... 560/40
(58) Field of Classification Search ................ 560/40
See application file for complete search history.

(56) References Cited

U.S. PATENT DOCUMENTS 4,535,177 A * 8/1985 Golec et al. .................. 560/38

OTHER PUBLICATIONS

Genji Iwasaki, Rieko Kimura, Naganori Numao, and Kiyosi Kondo□□A stereoselective synthesis of N-[(S)-1-Ethoxycarbonyl-3-phenyl propyl]-L-alanine Derivatives by Means of Reductive Amination□□Chemistry Letters pp. 1691-1694,1988.*
Barney, CL et al., Tetrahedron Letters, p. 5547-5550 (1990), "A Convenient Synthesis of Hindered Amines and alpha-Trifluoromethylamines from Ketones".
Ikota, K et al., Chemical and Pharmaceutical Bulletin, p. 887-894 (1983), "Stereochemical Studies LIX. Asymmetric Transamination from (S)-alpha-Amino Acids. Synthesis of (S)-alpha-Amino Acid Esters to Ketones".
Harada, K et al., Bulletin of Chemical Society of Japan, p. 1367-1370 (1984), "Asymmetric Hydrogenation of Schiff Base Prepared from alpha-Keto Ester with Aliphatic Amino Acid Ester".
Blacklock, TJ et al., Journal of Organic Chemistry, p. 836-844 (1988), "Synthesis of Semisynthetic Dipeptides Using N-Carboxyanhydrides and Chiral Induction on Raney Nickel. A Method Practical for Large Scale".

* cited by examiner

*Primary Examiner*—Samuel A Barts
*Assistant Examiner*—Lalitha Nagubandi
(74) *Attorney, Agent, or Firm*—Nicole M. Beeler; Mark R. Daniel

(57) ABSTRACT

This invention describes a reductive amination process whereby perfluorinated ketones or ketals are combined with α-aminoesters under basic conditions to form metal carboxylates. Diastereoselective reductions of the metal carboxylates enable access to two diastereomers, depending on the reducing conditions.

10 Claims, No Drawings

DIASTEREOSELECTIVE REDUCTIVE AMINATION PROCESS

PRIORITY CLAIM

This application is claims priority to U.S. Provisional Application Ser. No. 60/598,603, filed Aug. 4, 2004.

BACKGROUND OF THE INVENTION

This invention describes a reductive amination process whereby perfluorinated ketones or ketals are combined with α-aminoesters under basic conditions to form imine metal carboxylates. Diastereoselective reductions of the imine metal carboxylates enable access to two diastereomers, depending on the reducing conditions. These diastereomers can be further substituted to provide selective cathepsin K inhibitors which can be used in the treatment of osteoporosis and osteoarthritis.

The art involved imines of amino esters, where as the instant invention involves imines of carboxylic acid salts. In addition, the previously reported substrates do not contain fluorinated imine substituents. The selectivities obtained under the conditions described herein are much higher than those presented in the art.

This invention solves two problems. What is needed in the art is a process for the formation of imines from ketones or ketals bearing fluorines in the alpha position. This is a difficult transformation due to the stability of an initially formed hemi aminal intermediate which is difficult to dehydrate to give the imine. This problem had previously been solved by using strongly acidic solutions and high temperatures, which generally leads to decomposition of the starting materials and low yields of the required imine. The process of this invention uses basic conditions for the imine formation and has a number of advantages, including: the imines are formed under much milder conditions (between 20 and 50° C. and the presence of $MeO^-M^+$ or $M^+{}_2CO_3{}^=$) which gives more efficient recovery (~90%); a wider range of substrates are tolerated by these conditions; and the imine product is a stable carboxylic acid salt which upon reduction can give a corresponding substituted amino acid product. This avoids a potentially problematic ester hydrolysis step which can lead to epimerization of the amino acid stereocenter. Also, by the careful choice of reducing conditions, the two amino acid diastereoisomers can be accessed from the same imine metal carboxylate.

SUMMARY OF THE INVENTION

By this invention, there are provided processes for the preparation of compounds of structural formulas IA and IB:

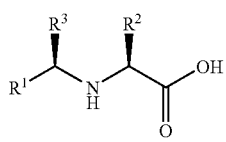

IA

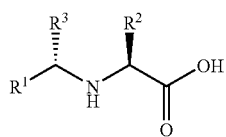

IB comprising the steps of:

a. Combining a ketone with an α-aminoester of formula II in the presence of a base and solvent to form an imine metal carboxylate of formula III, and

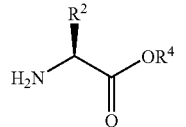

II

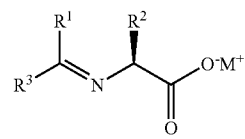

III b. Reducing the imine metal carboxylate of formula III to produce a compound of formula IA or IB;

wherein $R^1$ is $C_{1-5}$ alkyl, $C_{3-8}$ cycloalkyl, aryl or heteroaryl;

$R^2$ is $C_{1-5}$ alkyl, $C_{1-5}$ haloalkyl, $C_{3-8}$ cycloalkyl, arylalkyl, aryl or heteroaryl;

$R^3$ $C_{1-5}$ alkyl, $C_{1-5}$ haloalkyl, $C_{3-8}$ cycloalkyl, aryl, heteroaryl, $CF_3$, $CHF_2$, $CH_2F$ or $C_2F_5$;

$R^4$ is $C_{1-5}$ alkyl;

M is hydrogen, lithium, sodium, potassium or cesium.

DETAILED DESCRIPTION OF THE INVENTION

By this invention, there are provided processes for the preparation of compounds of structural formulas IA and IB:

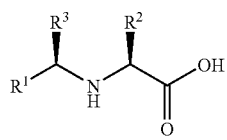

IA

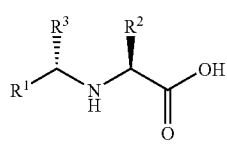

IB comprising the steps of:

a. Combining a ketone or ketal with an α-aminoester of formula II in the presence of a base and solvent to form an imine metal carboxylate of formula III, and

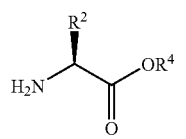

II

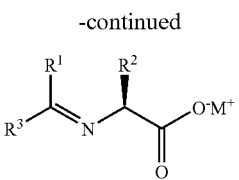

b. Reducing the imine metal carboxylate of formula III to produce a compound of formula IA or IB;

wherein $R^1$ is $C_{1-5}$ alkyl, $C_{3-8}$ cycloalkyl, aryl or heteroaryl;
$R^2$ is $C_{1-5}$ alkyl, $C_{1-5}$ haloalkyl, $C_{3-8}$ cycloalkyl, arylalkyl, aryl or heteroaryl;
$R^3$ $C_{1-5}$ alkyl, $C_{1-5}$ haloalkyl, $C_{3-8}$ cycloalkyl, aryl, heteroaryl, $CF_3$, $CHF_2$, $CH_2F$ or $C_2F_5$;
$R^4$ is $C_{1-5}$ alkyl;
M is hydrogen, lithium, sodium, potassium or cesium.

In an embodiment of the invention, $R^3$ is $CF_3$, $CHF_2$, $CH_2F$ or $C_2F_5$.

In an embodiment of the invention, M is potassium.

A ketone or ketal is combined with an α-aminoester of formula II in the presence of a base and solvent to form an imine metal carboxylate of formula III. In one class of the invention, the base is a metal carbonate or alkoxide, and the solvent is an alcohol, an ether, an ester or an amide. In one subclass of the invention the alcohol is methanol, ethanol, 1-propanol, 2-propanol, trifluoroethanol, butanol, isoamylalcohol, 2-methoxththanol or mixtures thereof. In one subclass of the invention, the ether is tetrahydrofuran (THF), diethyl ether, diisopropyl ether, dibutyl ether, t-butylmethyl ether (TBME), dimethoxyethane, or mixtures thereof. In one subclass of the invention, the ester is ethyl acetate, propyl acetate, isopropyl acetate, butyl acetate, ethyl propionate, or mixtures thereof. In one subclass of the invention, the amide is dimethylformamide (DMF), dimethylacetamide (DMAC), 1-methyl-2-pyrrolidinone (NMP), 1,3-dimethyl-3,4,5,6-tetrahydro-2(1H)-pyrimnidinone, or mixtures thereof. In one embodiment of the invention, the base is potassium carbonate, potassium methoxide or potassium phosphate and the solvent is methanol. In one class of the invention, this combination is performed at a temperature of about 15° C. to about 80° C. In a subclass of the invention, the temperature is about 30° C. to about 60° C.

In one aspect of the invention, the imine metal carboxylate of formula III is not isolated, and the reduction is performed with a metal borohydride prepared in an ether solvent to yield a compound of formula IA. In a class of the invention, the metal borohydride is calcium borohydride, magnesium borohydride, zinc borohydride or zirconium borohydride. In a subclass of the invention, the metal borohydride is zinc borohydride. In a class of the invention, the ether solvent is tetrahydrofuran (THF), diethyl ether, diisopropyl ether, dibutyl ether, t-butylmethyl ether (TBME), dimethoxyethane, ethyleneglycoldimethyl ether or mixtures thereof. In another class of the invention, a co-solvent is added to the ether solvent. In a further class of the invention, the co-solvent is $C_{1-4}$ alkyl nitrie or aryl nitrile. In a subclass of the invention, the co-solvent is acetonitrile. In a class of the invention, the volume of co-solvent is 50–95 vol %. In a subclass of the invention, the volume of co-solvent is 85–95 vol %.

In a class of the invention, the reduction is performed at a temperature of about 25° C. to about –40° C. to yield a compound of formula IA. In a subclass of the invention, the reduction is performed at a temperature of about 0° C. to about –40° C. to yield a compound of formula IA.

In another aspect of the invention the reduction of the metal carboxylate of formula III is performed with a metal borohydride in a solvent to yield a compound of formula IB. In a class of the invention, the metal borohydride is lithium borohydride, sodium borohydride or potassium borohydride. In a subclass of the invention, the metal borohydride is sodium borohydride. In a class of the invention the solvent is tetrahydrofuran. In a class of the invention water is added as a cosolvent in a volume of 1–10%. In a class of the invention the reduction is performed at a temperature of about 25° C. to about 0° C.

In another aspect of the invention, the reduction is performed with hydrogen and a chiral metal catalyst to yield a compound of formula IB. In one class of the invention, the chiral metal catalyst is derived from an Iridium, Rhodium or Ruthenium complex and a phosphine ligand. In a subclass of the invention, the chiral metal catalyst is (phanephos)Rh(COD)Cl or (i-Pr-ferrolane)Rh(COD)Cl.

In another aspect of the invention, the reduction is performed with a boron hydride and a chiral Lewis acid catalyst to yield a compound of formula IB. In one class of the invention, boron hydride is catechol borane. In another aspect of the invention, the chiral Lewis acid catalyst is a $C_{1-4}$ alkyl-CBS-oxazaborolidine. In a subclass of the invention, the chiral Lewis acid catalyst is methyl-CBS-oxazaborolidine.

By this invention, there are provided processes for the preparation of compounds of structural formulas IC and ID:

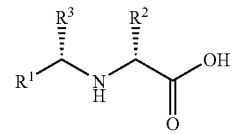

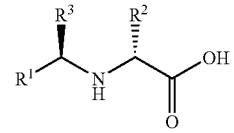

comprising the steps of:
a. Combining a ketone or ketal with an α-aminoester of formula IV in the presence of a base and solvent to form an imine metal carboxylate of formula V, and

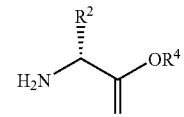

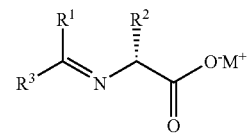

b. Reducing the imine metal carboxylate of formula V to produce a compound of formula IC or ID;

wherein $R^1$ is $C_{1-5}$ alkyl, $C_{3-8}$ cycloalkyl, aryl or heteroaryl;

$R^2$ is $C_{1-5}$ alkyl, $C_{1-5}$ haloalkyl, $C_{3-8}$ cycloalkyl, arylalkyl, aryl or heteroaryl;

$R^3$ $C_{1-5}$ alkyl, $C_{1-5}$ haloalkyl, $C_{3-8}$ cycloalkyl, aryl, heteroaryl, $CF_3$, $CHF_2$, $CH_2F$ or $C_2F_5$;

$R^4$ is $C_{1-5}$ alkyl;

M is hydrogen, lithium, sodium, potassium or cesium.

In an embodiment of the invention, $R^3$ is $CF_3$, $CHF_2$, $CH_2F$ or $C_2F_5$.

In an embodiment of the invention, M is potassium.

A ketone or ketal is combined with an α-aminoester of formula IV in the presence of a base and solvent to form an imine metal carboxylate of formula V. In one class of the invention, the base is a metal carbonate or alkoxide, and the solvent is an alcohol, an ether, an ester or an amide. In one subclass of the invention the alcohol is methanol, ethanol, 1-propanol, 2-propanol, trifluoroethanol, butanol, isoamylalcohol, 2-methoxththanol or mixtures thereof. In one subclass of the invention, the ether is tetrahydrofuran (THF), diethyl ether, diisopropyl ether, dibutyl ether, t-butylmethyl ether (TBME), dimethoxyethane, or mixtures thereof. In one subclass of the invention, the ester is ethyl acetate, propyl acetate, isopropyl acetate, butyl acetate, ethyl propionate, or mixtures thereof. In one subclass of the invention, the amide is dimethylformamide (DMF), dimethylacetamide (DMAC), 1-methyl-2-pyrrolidinone (NMP), 1,3-dimethyl-3,4,5,6-tetrahydro-2(1H)-pyrimidinone, or mixtures thereof. In one embodiment of the invention, the base is potassium carbonate or potassium methoxide and the solvent is methanol. In one class of the invention, this combination is performed at a temperature of about 15° C. to about 80° C. In a subclass of the invention, the temperature is about 30° C. to about 60° C.

In one aspect of the invention, the imine metal carboxylate of formula V is not isolated, and the reduction is performed with a metal borohydride prepared in an ether solvent to yield a compound of formula IC. In a class of the invention, the metal borohydride is calcium borohydride, magnesium borohydride, zinc borohydride or zirconium borohydride. In a subclass of the invention, the metal borohydride is zinc borohydride. In a class of the invention, the ether solvent is tetrahydrofuran (THF), diethyl ether, diisopropyl ether, dibutyl ether, t-butylmethyl ether (TBME), dimethoxyethane, ethyleneglycoldimethyl ether or mixtures thereof. In another class of the invention, a co-solvent is added to the ether solvent. In a further class of the invention, the co-solvent is $C_{1-4}$ alkyl nitrile or aryl nitrile. In a subclass of the invention, the co-solvent is acetonitrile. In a class of the invention, the volume of co-solvent is 50–95 vol %. In a subclass of the invention, the volume of co-solvent is 85–95 vol %.

In a class of the invention, the reduction is performed at a temperature of about 25° C. to about −40° C. to yield a compound of formula IC. In a subclass of the invention, the reduction is performed at a temperature of about 0° C. to about −40° C. to yield a compound of formula IA.

In another aspect of the invention the reduction of metal carboxylate of formula V is performed with a metal borohydride in a solvent to yield a compound of formula ID. In a class of the invention, the metal borohydride is lithium borohydride, sodium borohydride or potassium borohydride. In a subclass of the invention, the metal borohydride is sodium borohydride. In a class of the invention the solvent is tetrahydrofuran. In a class of the invention water is added as a cosolvent in a volume of 1–10%. In a class of the invention the reduction is performed at a temperature of about 25° C. to about 0° C.

In another aspect of the invention, the reduction is performed with hydrogen and a chiral metal catalyst to yield a compound of formula ID. In one class of the invention, the chiral metal catalyst is derived from an Iridium, Rhodium or Ruthenium complex and a phosphine ligand. In a subclass of the invention, the chiral metal catalyst is (phanephos)Rh(COD)Cl or (i-Pr-ferrolane)Rh(COD)Cl.

In another aspect of the invention, the reduction is performed with a boron hydride and a chiral Lewis acid catalyst to yield a compound of formula ID. In one class of the invention, boron hydride is catechol borane. In another aspect of the invention, the chiral Lewis acid catalyst is a $C_{1-4}$ alkyl-CBS-oxazaborolidine. In a subclass of the invention, the chiral Lewis acid catalyst is methyl-CBS-oxazaborolidine.

The term "alkyl" as used herein shall mean a substituting univalent group derived by conceptual removal of one hydrogen atom from a straight or branched-chain acyclic saturated hydrocarbon (i.e., $-CH_3$, $-CH_2CH_3$, $-CH_2CH_2CH_3$, $-CH(CH_3)_2$, $-CH_2CH_2CH_2CH_3$, $-CH_2CH(CH_3)_2$, $-C(CH_3)_3$, etc.).

The term "cycloalkyl" shall mean cyclic rings of alkanes of three to eight total carbon atoms, unless otherwise indicated, or any number within this range (i.e., cyclopropyl, cyclobutyl, cyclopentyl, cyclohexyl, cycloheptyl or cyclooctyl).

As used herein, "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As appreciated by those of skill in the art, "halo" or "halogen" as used herein is intended to include chloro, fluoro, bromo and iodo. The term "keto" means carbonyl (C=O). The term "alkoxy" as used herein means an alkyl portion, where alkyl is as defined above, connected to the remainder of the molecule via an oxygen atom. Examples of alkoxy include methoxy, ethoxy and the like.

The term "haloalkyl" means an alkyl radical as defined above, unless otherwise specified, that is substituted with one to five, preferably one to three halogen. Representative examples include, but are not limited to trifluoromethyl, dichloroethyl, and the like.

The term "arylalkyl" includes an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, and chlorophenylethyl. Examples of alkylaryl include, but are not limited to, toluyl, ethylphenyl, and propylphenyl.

In the schemes and examples below, various reagent symbols and abbreviations have the following meanings:

| | |
|---|---|
| CH₃CN: | Acteonitrile |
| DCHA: | Dicyclohexylamine |
| HCl: | Hydrochloric acid |
| K₂CO₃: | Potassium carbonate |
| MeOH: | Methanol |
| TBME: | t-Butyl methyl ether |
| THF: | Tetrahydrofuran |
| Zn(BH₄)₂: | Zinc Borohydride |
| NaBH₄ | Sodium Borohydride |

Schemes 1 and 2 depict the condensation of an alpha-aminoester with a ketone or ketal under basic conditions leads to the formation of a stable isolable imine carboxylate in high yield. Subsequent treatment of the imine under selected reducing conditions provides access to either the syn or anti diasteoisomer of the corresponding substituted amino acid in high yield and selectivity. Thus this methodology can provide easy access to all four diastereoisomers of a substituted amino acid by judicious choice of alpha-aminoester enantiomer and reducing conditions.

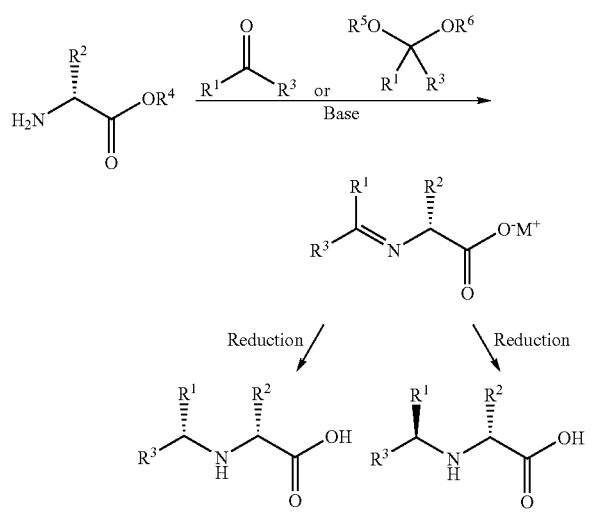

R5 and R6 are each independently hydrogen or alkyl.

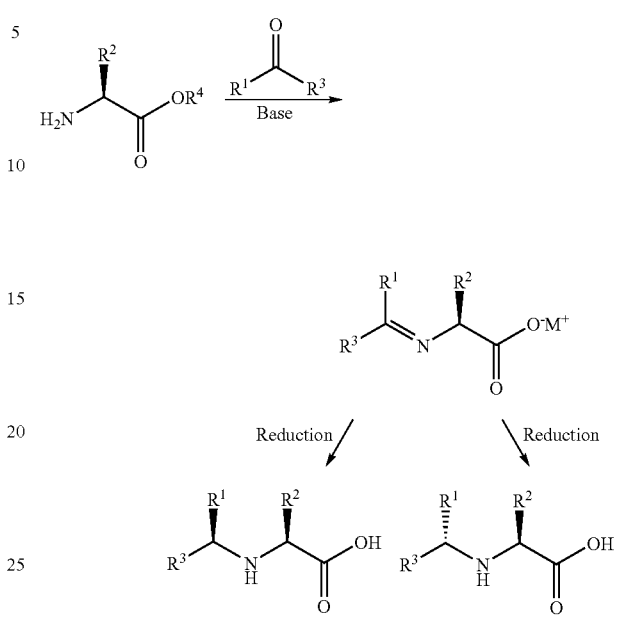

The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

EXAMPLE 1

N-(2,2,2-TRIFLUORO-1-PHENYLETHYLIDENE)-L-VALINE POTASSIUM SALT 2,2,2-Trifluoroacetophenone (4.24 g, 24.3 mmol) was added to a mixture of L-valine ethyl ester (3.21 g, 22.1 mmol) and K₂CO₃ (2.90 g, 20.9 mmol) in MeOH (50 mL). The mixture was warmed to 50° C. for 18 h. The mixture was cooled to 20–25° C., filtered and concentrated. The residue was suspended in TBME (100 ml) and filtered to give the title compound as a white solid.

EXAMPLE 2

N-(2,2,2-TRIFLUORO-1-PHENYLETHYLIDENE)-L-LEUCINE POTASSIUM SALT

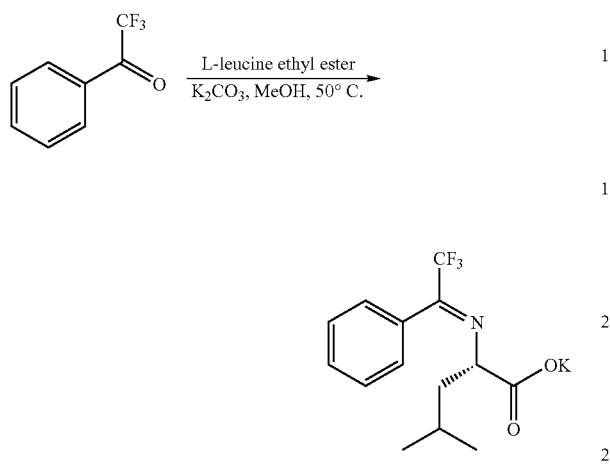

2,2,2-Trifluoroacetophenone (4.24 g, 24.3 mmol) was added to a mixture of L-leucine ethyl ester (3.52 g, 22.1 mmol) and $K_2CO_3$ (2.90 g, 20.9 mmol) in MeOH (50 mL). The mixture was warmed to 50° C. for 18 h. The mixture was cooled to 20–25° C., filtered and concentrated. The residue was suspended in TBME (100 ml) and filtered to give the title compound as a white solid.

EXAMPLE 3

4-FLUORO-N-(2,2,2-TRIFLUORO-1-PHENYL-ETHYL)-L-LEUCINE POTASSIUM SALT

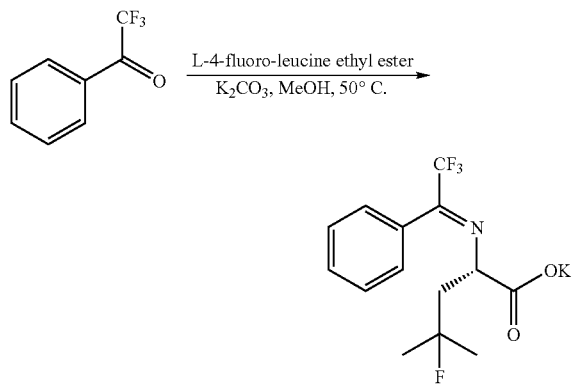

2,2,2-Trifluoroacetophenone (4.24 g, 24.3 mmol) was added to a mixture of L-4-fluoro-leucine ethyl ester (3.92 g, 22.1 mmol) and $K_2CO_3$ (2.90 g, 20.9 mmol) in MeOH (50 mL). The mixture was warmed to 50° C. for 18 h. The mixture was cooled to 20–25° C., filtered and concentrated. The residue was suspended in TBME (100 ml) and filtered to give the title compound as a white solid.

EXAMPLE 4

N-(2,2,2-TRIFLUORO-1-PHENYLETH-YLIDENE)-L-PHENYLALININE-POTASSIUM SALT

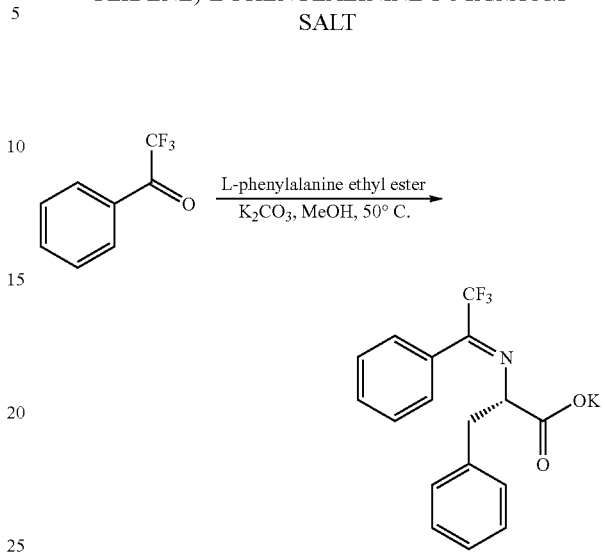

2,2,2-Trifluoroacetophenone (4.24 g, 24.3 mmol) was added to a mixture of L-phenylalinine ethyl ester (4.27 g, 22.1 mmol) and $K_2CO_3$ (2.90 g, 20.9 mmol) in MeOH (50 mL). The mixture was warmed to 50 ° C. for 18 h. The mixture was cooled to 20–25° C., filtered and concentrated. The residue was suspended in TBME (100 ml) and filtered to give the title compound as a white solid.

EXAMPLE 5

(2S)-2-{[(1Z)-2,2,2-TRIFLUORO-1-PHENYLETH-YLIDENE]AMINO}BUTANOIC ACID POTAS-SIUM SALT

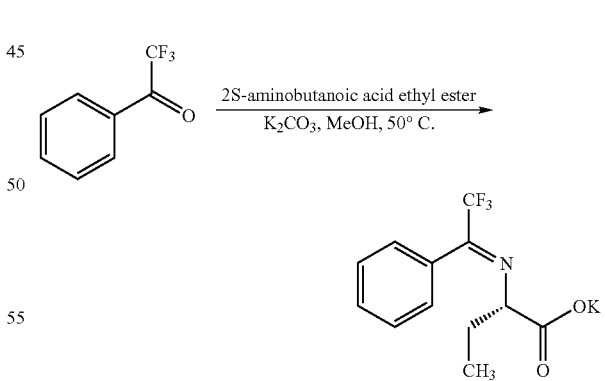

2,2,2-Trifluoroacetophenone (4.24 g, 24.3 mmol) was added to a mixture of 2S-aminobutanoic acid ethyl ester (2.90 g, 22.1 mmol) and $K_2CO_3$ (2.90 g, 20.9 mmol) in MeOH (50 mL). The mixture was warmed to 50° C. for 18 h. The mixture was cooled to 20–25° C., filtered and concentrated. The residue was suspended in TBME (100 ml) and filtered to give the title compound as a white solid.

EXAMPLE 6

N-(2,2,2-TRIFLUORO-1-PHENYLETHYLIDENE)-L-ALININE POTASSIUM SALT

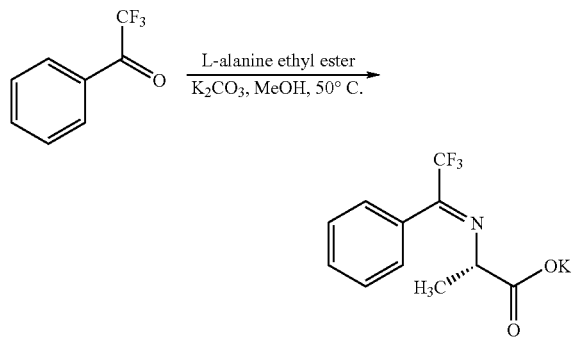

2,2,2-Trifluoroacetophenone (4.24 g, 24.3 mmol) was added to a mixture of L-alinine ethyl ester (2.59 g, 22.1 mmol) and $K_2CO_3$ (2.90 g, 20.9 mmol) in MeOH (50 mL). The mixture was warmed to 50° C. for 18 h. The mixture was cooled to 20–25° C., filtered and concentrated. The residue was suspended in TBME (100 ml) and filtered to give the title compound as a white solid.

EXAMPLE 7

N-[(1R)-2,2,2-TRIFLUORO-1-PHENETHYL]-L-VALINE

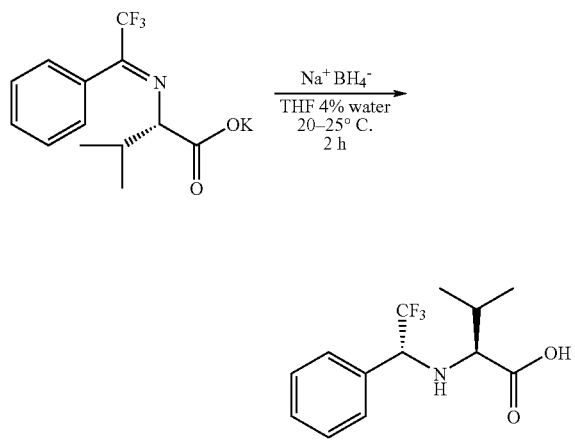

N-(2,2,2-Trifluoro-1-phenylethylidene)-L-valine potassium salt (50 mg, 0.161 mmol) was combined with sodium borohydride (24.3 mg, 0.642 mmol). THF (1.0 ml) and water (40 ul) were added to this mixture and the reaction was stirred at 20–25° C. for 1 h. The reaction was quenched with 1N NaOH (2 ml) and the aqueous layer extracted once with TBME. The aqueous layer was acidified with 1N HCl (5 ml)) and extracted with TBME (2×10 ml). The organic layer was washed with brine (5 ml), dried over $Na_2SO_4$, and concentrated to yield the title compound as a white solid. $^{19}F$ NMR of the product indicated a diastereomeric ratio of 65:1.

EXAMPLE 8

N-[(1R)-2,2,2-TRIFLUORO-1-PHENETHYL]-L-LEUCINE

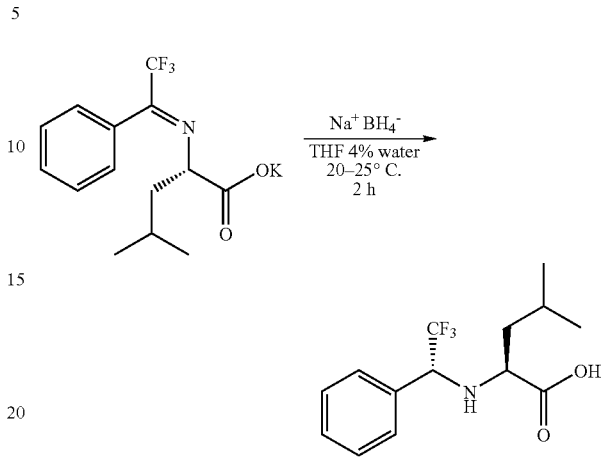

N-(2,2,2-Trifluoro-1-phenylethylidene)-L-leucine potassium salt (50 mg, 0.154 mmol) was combined with sodium borohydride (23.3 mg, 0.615 mmol). THF (1.0 ml) and water (40 ul) were added to this mixture and the reaction was stirred at 20–25° C. for 1 h. The reaction was quenched with 1N NaOH (2 ml) and the aqueous layer extracted once with TBME. The aqueous layer was acidified with 1N HCl (5 ml)) and extracted with TBME (2×10 ml). The organic layer was washed with brine (5 ml), dried over $Na_2SO_4$, and concentrated to yield the title compound as a white solid. $^{19}F$ NMR of the product indicated a diastereomeric ratio of 59:1.

EXAMPLE 9

4-FLUORO-N-[(1R)-2,2,2-TRIFLUORO-1-PHENETHYL]-L-LEUCINE

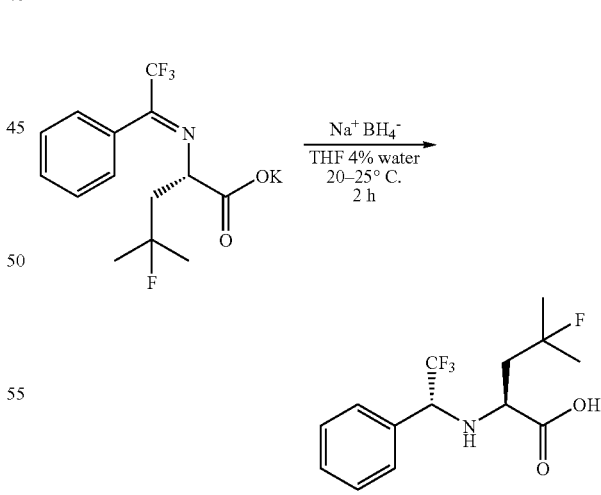

4-Fluoro-N-(2,2,2-Trifluoro-1-phenylethylidene)-L-leucine potassium salt (50 mg, 0.146 mmol) was combined with sodium borohydride (22.0 mg, 0.582 mmol). THF (1.0 ml) and water (40 ul) were added to this mixture and the reaction was stirred at 20–25° C. for 1 h. The reaction was quenched with 1N NaOH (2 ml) and the aqueous layer extracted once with TBME. The aqueous layer was acidified with 1N HCl (5 ml)) and extracted with TBME (2×10 ml). The organic layer was washed with brine (5 ml), dried over Na$_2$SO$_4$, and concentrated to yield the title compound as a white solid. $^{19}$F NMR of the product indicated a diastereomeric ratio of 71:1.

EXAMPLE 10

N-[(1R)-2,2,2-TRIFLUORO-1-PHENETHYL]-L-PHENYLALININE

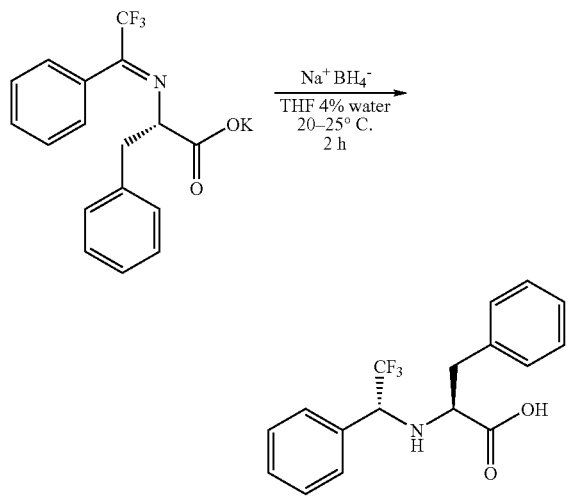

N-(2,2,2-Trifluoro-1-phenylethylidene)-L-phenylalinine potassium salt (50 mg, 0.139 mmol) was combined with sodium borohydride (21.1 mg, 0.557 mmol). THF (1.0 ml) and water (40 ul) were added to this mixture and the reaction was stirred at 20–25° C. for 1 h. The reaction was quenched with 1N NaOH (2 ml) and the aqueous layer extracted once with TBME. The aqueous layer was acidified with 1N HCl (5 ml)) and extracted with TBME (2×10 ml). The organic layer was washed with brine (5 ml), dried over Na$_2$SO$_4$, and concentrated to yield the title compound as a white solid. $^{19}$F NMR of the product indicated a diastereomeric ratio of 61:1.

EXAMPLE 11

N-[(1R)-2,2,2-TRIFLUORO-1-PHENETHYL]-L-ETHYLGLYCINE

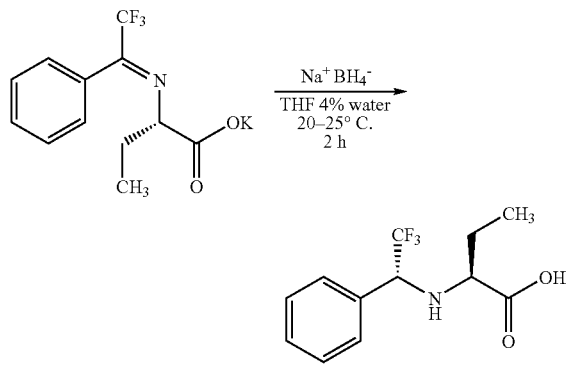

(2S)-2-{[(1Z)-2,2,2-trifluoro-1-phenylethylidene] amino}butanoic acid potassium salt (50 mg, 0.168 mmol) was combined with sodium borohydride (25.4 mg, 0.673 mmol). THF (1.0 ml) and water (40 ul) were added to this mixture and the reaction was stirred at 20–25° C. for 1 h. The reaction was quenched with 1N NaOH (2 ml) and the aqueous layer extracted once with TBME. The aqueous layer was acidified with 1N HCl (5 ml)) and extracted with TBME (2×10 ml). The organic layer was washed with brine (5 ml), dried over Na$_2$SO$_4$, and concentrated to yield the title compound as a white solid. $^{19}$F NMR of the product indicated a diastereomeric ratio of 20:1.

EXAMPLE 12

N-[(1R)-2,2,2-TRIFLUORO-1-PHENETHYL]-L-ALININE

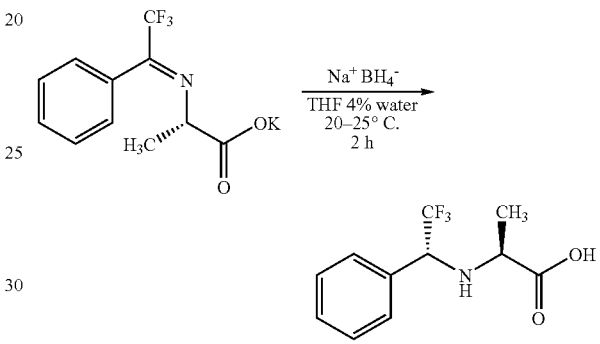

N-(2,2,2-Trifluoro-1-phenylethylidene)-L-ethylalinine potassium salt (50 mg, 0.176 mmol) was combined with sodium borohydride (26.7 mg, 0.706 mmol). THF (1.0 ml) and water (40 ul) were added to this mixture and the reaction was stirred at 20–25° C. for 1 h. The reaction was quenched with 1N NaOH (2 ml) and the aqueous layer extracted once with TBME. The aqueous layer was acidified with 1N HCl (5 ml)) and extracted with TBME (2×10 ml). The organic layer was washed with brine (5 ml), dried over Na$_2$SO$_4$, and concentrated to yield the title compound as a white solid. $^{19}$F NMR of the product indicated a diastereomeric ratio of 6:1.

EXAMPLE 13

N-[(1S)-2,2,2-TRIFLUORO-1-PHENETHYL]-L-VALINE

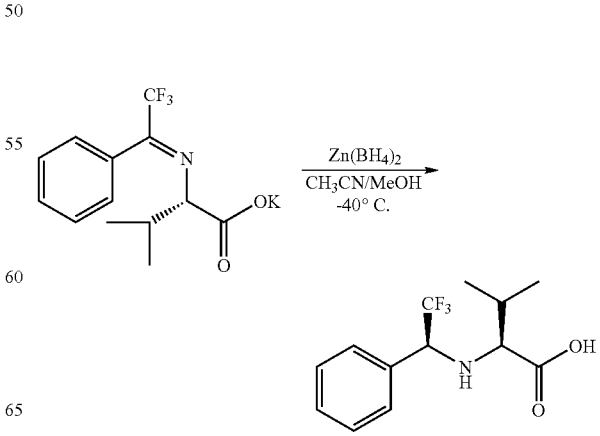

Zinc (II) chloride (204 mg, 1.5 mmol) and sodium borohydride (113 mg, 3.0 mmol) were suspended in DME (1.5 mL) and stirred for 18 h. The resulting suspension was cooled to −40° C. and a suspension of N-(2,2,2-trifluoro-1-phenylethylidene)-L-valine potassium salt (311 mg, 1.0 mmol) in CH₃CN (15 ml) and MeOH (1.5 ml) was added. After 3 h 1N HCl (20 ml) was added and the mixture was extracted with TBME (3×20 ml). The organic layers were washed with brine (10 ml), dried over Na₂SO₄, filtered and concentrated to give the title compound as a white solid. ¹⁹F NMR of the product indicated a diastereomeric ratio of 33:1.

EXAMPLE 14

N-[(1S)-2,2,2-TRIFLUORO-1-PHENETHYL]-L-LEUCINE

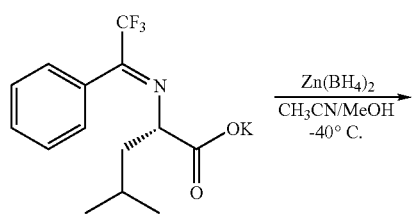

Zinc (II) chloride (204 mg, 1.5 mmol) and sodium borohydride (113 mg, 3.0 mmol) were suspended in DME (1.5 mL) and stirred for 18 h. The resulting suspension was cooled to −40° C. and a suspension of N-(2,2,2-trifluoro-1-phenylethylidene)-L-leucine potassium salt (325 mg, 1.0 mmol) in CH₃CN (15 ml) and MeOH (1.5 ml) was added. After 3 h 1N HCl (20 ml) was added and the mixture was extracted with TBME (3×20 ml). The organic layers were washed with brine (10 ml), dried over Na₂SO₄, filtered and concentrated to give the title compound as a white solid. ¹⁹F NMR of the product indicated a diastereomeric ratio of 18:1.

EXAMPLE 15

4-FLUORO-N-[(1S)-2,2,2-TRIFLUORO-1-PHENETHYL]-L-LEUCINE

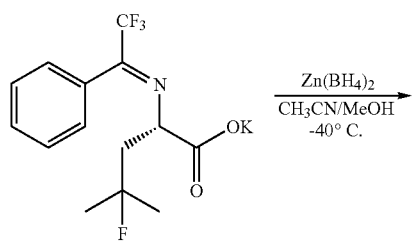

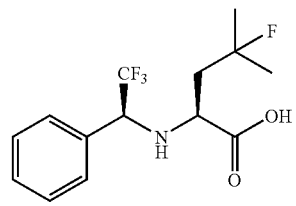

Zinc (II) chloride (204 mg, 1.5 mmol) and sodium borohydride (113 mg, 3.0 mmol) were suspended in DME (1.5 mL) and stirred for 18 h. The resulting suspension was cooled to −40° C. and a suspension of 4-fluoro-N-(2,2,2-trifluoro-1-phenylethylidene)-L-leucine potassium salt (343 mg, 1.0 mmol) in CH₃CN (15 ml) and MeOH (1.5 ml) was added. After 3 h 1N HCl (20 ml) was added and the mixture was extracted with TBME (3×20 ml). The organic layers were washed with brine (10 ml), dried over Na₂SO₄, filtered and concentrated to give the title compound as a white solid. ¹⁹F NMR of the product indicated a diastereomeric ratio of 25:1.

EXAMPLE 16

N-[(1S)-2,2,2-TRIFLUORO-1-PHENETHYL]-L-PHENYLALININE

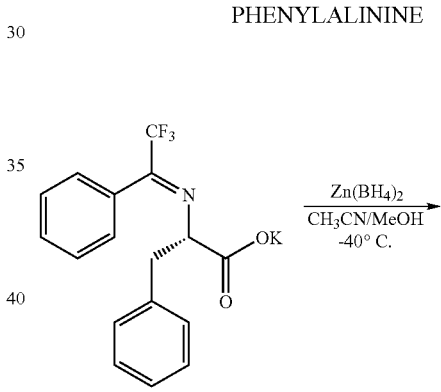

Zinc (II) chloride (204 mg, 1.5 mmol) and sodium borohydride (113 mg, 3.0 mmol) were suspended in DME (1.5 mL) and stirred for 18 h. The resulting suspension was cooled to −40° C. and a suspension of N-(2,2,2-trifluoro-1-phenylethylidene)-L-phenylalinine potassium salt (359 mg, 1.0 mmol) in CH₃CN (15 ml) and MeOH (1.5 ml) was added. After 3 h 1N HCl (20 ml) was added and the mixture was extracted with TBME (3×20 ml). The organic layers were washed with brine (10 ml), dried over Na₂SO₄, filtered and concentrated to give the title compound as a white solid. ¹⁹F NMR of the product indicated a diastereomeric ratio of 17:1.

EXAMPLE 17

BUTANOIC ACID, 2-{[(1S)-2,2,2-TRIFLUORO-1-PHENYLETHYLAMINO]-, (2S)-

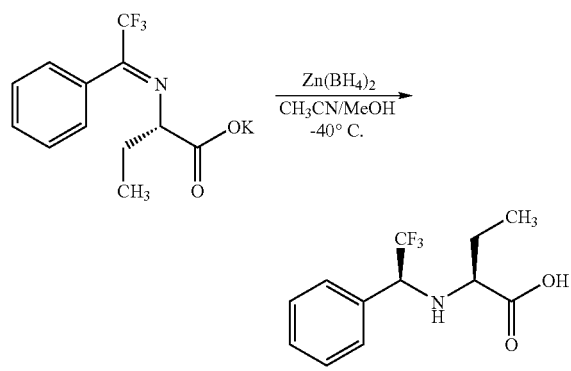

Zinc (II) chloride (204 mg, 1.5 mmol) and sodium borohydride (113 mg, 3.0 mmol) were suspended in DME (1.5 mL) and stirred for 18 h. The resulting suspension was cooled to −40° C. and a suspension of (2S)-2-{[(1Z)-2,2,2-trifluoro-1-phenylethylidene]amino}butanoic acid potassium salt (297 mg, 1.0 mmol) in CH$_3$CN (15 ml) and MeOH (1.5 ml) was added. After 3 h 1N HCl (20 ml) was added and the mixture was extracted with TBME (3×20 ml). The organic layers were washed with brine (10 ml), dried over Na$_2$SO$_4$, filtered and concentrated to give the title compound as a white solid. $^{19}$F NMR of the product indicated a diastereomeric ratio of 11:1.

EXAMPLE 18

N-[(1S)-2,2,2-TRIFLUORO-1-PHENETHYL]-L-ALININE

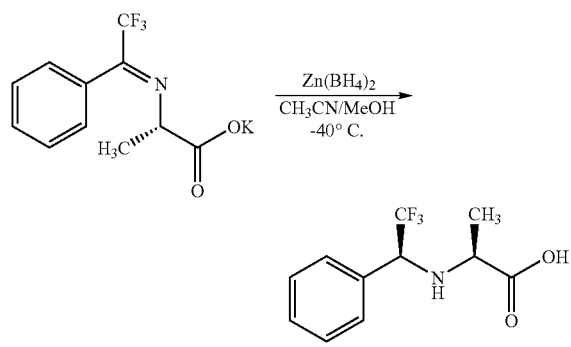

Zinc (II) chloride (204 mg, 1.5 mmol) and sodium borohydride (113 mg, 3.0 mmol) were suspended in DME (1.5 mL) and stirred for 18 h. The resulting suspension was cooled to −40° C. and a suspension of N-(2,2,2-trifluoro-1-phenylethylidene)-L-alinine potassium salt (283 mg, 1.0 mmol) in CH$_3$CN (15 ml) and MeOH (1.5 ml) was added. After 3 h 1N HCl (20 ml) was added and the mixture was extracted with TBME (3×20 ml). The organic layers were washed with brine (10 ml), dried over Na$_2$SO$_4$, filtered and concentrated to give the title compound as a white solid. $^{19}$F NMR of the product indicated a diastereomeric ratio of 6:1.

EXAMPLE 19

4-FLUORO-N-{(1S)-2,2,2-TRIFLUORO-1-[4'-(METHYLSULFONYL)BIPHENYL-4-YL]ETHYL}-L-LEUCINE DICYCLOHEXYLAMINE SALT

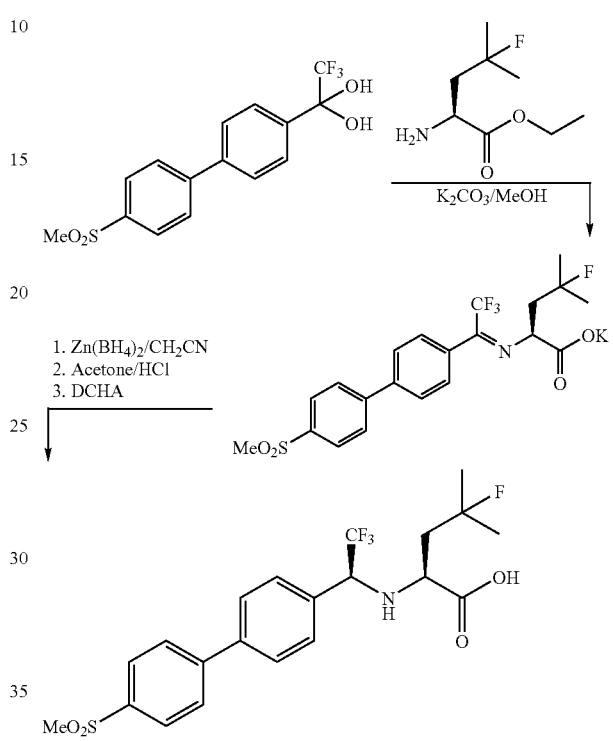

A 200 mL vessel was charged with 2,2,2-trifluoro-1-[4'-(methylsulphonyl)biphenyl-4-yl]ethane-1,1-diol (9.08 g, 26.2 mmol), F-leucine ethyl ester sulphate salt (8.66 g, 31.5 mmol), potassium carbonate (14.5 g, 104.9 mmol) and methanol (27.3 mL). The mixture was heated to 50° C., aged for 4 h and then cooled to −5° C.

A 500 mL vessel was charged with zinc chloride (7.15 g, 52.5 mmol) and dimethoxyethane (40.9 mL). The mixture was cooled to −10° C. and sodium borohydride (3.97 g, 104.9 mmol) charged in a portionwise manner. The mixture was aged at −10° C. for 1 h and acetonitrile (63.6 mL) added, maintaining the temperature below 0° C.

The imine mixture was then transferred to the borohydride solution, at such a rate as to maintain the temperature between −5 and +5° C. The reaction was then aged between −5 and +5° C. for 1.5 h, quenched by the slow addition of acetone (33.9 mL) and allowed to warm to 20° C. TBME (60.6 mL), 2M HCl (181.7 mL) and DI Water (63.6 mL) were charged and the mixture aged for 30 min. The organic phase was separated and the aqueous re-extracted with TBME (45.4 mL). The two TBME phases were combined, washed with water (45.4 mL×4) and diluted with TBME (139.3 mL). Dicyclohexylamine (5.23 g, 28.8 mmol) was then charged over 30 min at 20° C. The product slurry was aged at 20° C. for 1 h, filtered and washed with TBME (36.3 mL). After drying in-vacuo at 30° C. to constant weight, the title compound was obtained as a white powder.

What is claimed is:

1. A process for preparing a compound of formula IA or IB:

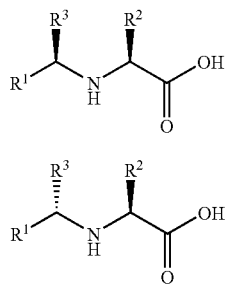

IA

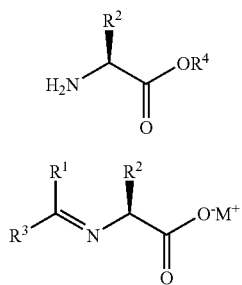

IB comprising the steps of:

a. Combining a ketone or ketal with an α-aminoester of formula II in the presence of a base and solvent to form an imine metal carboxylate of formula III, and

II

III b. Reducing the imine metal carboxylate of formula III to produce a compound of formula IA or IB;

wherein $R^1$ is $C_{1-5}$ alkyl, $C_{3-8}$ cycloalkyl, aryl or heteroaryl;

$R^2$ is $C_{1-5}$ alkyl, $C_{1-5}$ haloalkyl, $C_{3-8}$ cycloalkyl, arylalkyl, aryl or heteroaryl;

$R^3$ $C_{1-5}$ alkyl, $C_{1-5}$ haloalkyl, $C_{3-8}$ cycloalkyl, aryl, heteroaryl, $CF_3$, $CHF_2$, $CH_2F$ or $C_2F_5$;

$R^4$ is $C_{1-5}$ alkyl;

M is hydrogen, lithium, sodium, potassium or cesium.

2. The process of claim 1 wherein the base is a metal carbonate or alkoxide, and the solvent is an alcohol, an ether, an ester or an amide.

3. The process of claim 2 wherein the base is potassium carbonate, potassium methoxide or potassium phosphate and the solvent is methanol.

4. The process of claim 1 wherein step a is performed at a temperature of about 15° C. to about 80° C.

5. The process of claim 4 wherein the temperature is about 30° C. to about 60° C.

6. The process of claim 1 wherein the imine metal carboxylate of formula III is not isolated, and the reduction is performed with a metal borohydride prepared in an ether solvent to yield a compound of formula IA.

7. The process of claim 6 wherein the metal borohydride is calcium borohydride, magnesium borohydride, zinc borohydride or zirconium borohydride and the ether solvent is tetrahydrofuran, diethyl ether, diisopropyl ether, dibutyl ether, t-butylmethyl ether, dimethoxyethane, ethyleneglycoldimethyl ether or mixtures thereof.

8. The process of claim 6 wherein a co-solvent is added in a volume of 50–95%.

9. The process of claim 8 wherein the co-solvent is $C_{1-4}$ alkyl or aryl nitrile.

10. The process of claim 1 wherein step b is performed at a temperature of about 25 to about −40° C.

* * * * *

UNITED STATES PATENT AND TRADEMARK OFFICE
CERTIFICATE OF CORRECTION

PATENT NO. : 7,183,425 B2  
APPLICATION NO. : 11/193798  
DATED : February 27, 2007  
INVENTOR(S) : Cheng Yi Chen et al.

Page 1 of 1

It is certified that error appears in the above-identified patent and that said Letters Patent is hereby corrected as shown below:

On the Title Page

Item (73) Assignee should read: Merck Frosst Canada Ltd.
Quebec, CA

Merck Sharp & Dohme Corp.
Rahway, NJ

Signed and Sealed this
Twenty-first Day of April, 2015

Michelle K. Lee
*Director of the United States Patent and Trademark Office*